United States Patent
Tanimu et al.

(10) Patent No.: US 11,123,715 B2
(45) Date of Patent: Sep. 21, 2021

(54) MESOPOROUS COMPOSITE CATALYSTS CONTAINING BISMUTH SILICATE AND TRANSITION METAL OXIDE

(71) Applicant: KING FAHD UNIVERSITY OF PETROLEUM AND MINERALS, Dhahran (SA)

(72) Inventors: Gazali Tanimu, Dhahran (SA); Abdullah M. Aitani, Dhahran (SA); Sachio Asaoka, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 21 days.

(21) Appl. No.: 16/692,255

(22) Filed: Nov. 22, 2019

(65) Prior Publication Data
US 2021/0154646 A1    May 27, 2021

(51) Int. Cl.
*B01J 23/843* (2006.01)
*B01J 21/08* (2006.01)
(Continued)

(52) U.S. Cl.
CPC .......... *B01J 23/8437* (2013.01); *B01J 21/08* (2013.01); *B01J 37/0201* (2013.01);
(Continued)

(58) Field of Classification Search
CPC .... B01J 23/8437; B01J 21/08; B01J 37/0201; B01J 37/0236; B01J 37/08; B01J 37/04;
(Continued)

(56) References Cited

U.S. PATENT DOCUMENTS

| 4,174,354 A | 11/1979 | Grasselli et al. |
| 7,632,777 B2 | 12/2009 | Teshigahara et al. |
| (Continued) | | |

FOREIGN PATENT DOCUMENTS

| CN | 10 1229510 | * 7/2008 | ............ B01J 21/16 |
| CN | 101229510 B | 9/2010 | |
| (Continued) | | | |

OTHER PUBLICATIONS

G. Tanimu et al., "Oxidative dehydrogenation of n-butane to butadiene catalyzed by new mesoporous mixed oxides NiO—(beta-Bi2O3)—Bi2SiO5/SBA-15 system." Molecular Catalysis 488, pp. 1-8. (Year: 2020).*

(Continued)

*Primary Examiner* — Patricia L. Hailey
(74) *Attorney, Agent, or Firm* — Oblon, McClelland, Maier & Neustadt, L.L.P.

(57) ABSTRACT

Composite catalysts having bismuth silicate(s) (e.g. $Bi_2SiO_5$) and transition metal oxide(s) (e.g. nickel oxide) impregnated on mesoporous silica supports such as SBA-15, mesoporous silica foam, and silica sol. Methods of making and characterizing the composite catalysts as well as processes for oxidatively dehydrogenating alkanes (e.g. n-butane) and/or alkenes (e.g. 1-butene, 2-butene) to corresponding dienes (e.g. butadiene) employing the composite catalysts are also described.

20 Claims, 1 Drawing Sheet

(51) Int. Cl.
  *B01J 37/02* (2006.01)
  *C07C 5/48* (2006.01)
  *B01J 37/08* (2006.01)
  *B01J 37/04* (2006.01)
  *B01J 23/745* (2006.01)
  *B01J 23/755* (2006.01)
  *B01J 23/75* (2006.01)

(52) U.S. Cl.
  CPC ........... *B01J 37/0236* (2013.01); *B01J 37/08* (2013.01); *C07C 5/48* (2013.01); *B01J 23/745* (2013.01); *B01J 23/75* (2013.01); *B01J 23/755* (2013.01); *B01J 37/04* (2013.01); *B01J 2231/76* (2013.01); *B01J 2523/54* (2013.01); *B01J 2523/842* (2013.01); *B01J 2523/845* (2013.01); *B01J 2523/847* (2013.01); *C07C 2521/08* (2013.01); *C07C 2523/18* (2013.01); *C07C 2523/20* (2013.01)

(58) Field of Classification Search
  CPC ........ B01J 23/745; B01J 23/75; B01J 23/755; B01J 2231/76; B01J 2523/54; B01J 2523/842; B01J 2523/845; B01J 2523/847; C07C 5/48; C07C 2521/08; C07C 2523/18; C07C 2523/20; C10G 49/04; C10G 47/04; C10G 47/10; C10G 47/12; C10G 2300/70
  USPC .................. 502/246, 258–260; 585/654, 661
  See application file for complete search history.

(56) References Cited

U.S. PATENT DOCUMENTS

2007/0045116 A1* 3/2007 Hung ................... C09D 5/4496
                                                              204/471
2007/0093672 A1* 4/2007 Ryu ........................ B01J 38/52
                                                              558/270
2015/0291778 A1* 10/2015 Musick ................... C09C 3/063
                                                              524/407

FOREIGN PATENT DOCUMENTS

| CN | 108479745 A | | 9/2018 | |
|---|---|---|---|---|
| CN | 10 8816243 | * | 11/2018 | ............ B01J 23/887 |
| CN | 108816243 A | | 11/2018 | |
| CN | 10 9020800 | * | 12/2018 | ........... C07C 51/235 |
| CN | 11 0128274 | * | 8/2019 | ............. B01J 23/18 |
| CN | 11 1330588 | * | 6/2020 | ............ B01J 23/887 |

OTHER PUBLICATIONS

Lei Yuan et al., "Low-temperature sintering of bismuth-doped glass with high fluorescence properties from mesoporous silica SBA-15." Ceramics International 46, pp. 1164-1170. (Year: 2020).*

Ling Zhang, et al., "Solar light photocatalysis using $Bi_2O_3/Bi_2SiO_5$ nanoheterostructures formed in mesoporous $SiO_2$ microspheres", Crystengcomm, vol. 15, Issue 46, Dec. 2013, pp. 10043-10048 (Abstract only).

Michele Back, et al., "$Bi_2SiO_5$@g—$SiO_2$ upconverting nanopartides: a bismuth-driven core-shell self-assembly mechanism", Nanoscale, vol. 11, No. 2, Jan. 3, 2019, pp. 675-687 (Abstract only).

Anil Kumar Reddy Police, et al., "Bismuth Modified Porous Silica Preparation, Characterization and Photocatalytic Activity Evaluation for Degradation of Isoproturon", Journal of Materials Science & Technology, vol. 29, No. 7, 2013, pp. 639-646.

Huan-Ling Wang, et al., "Bismuth-Containing SBA-15 Mesoporous Silica Catalysts for Solvent-Free Liquid-Phase Oxidation of Cyclohexane by Molecular Oxygen", Helvetica Chimica Acta, vol. 90, 2007, pp. 1837-1847.

* cited by examiner

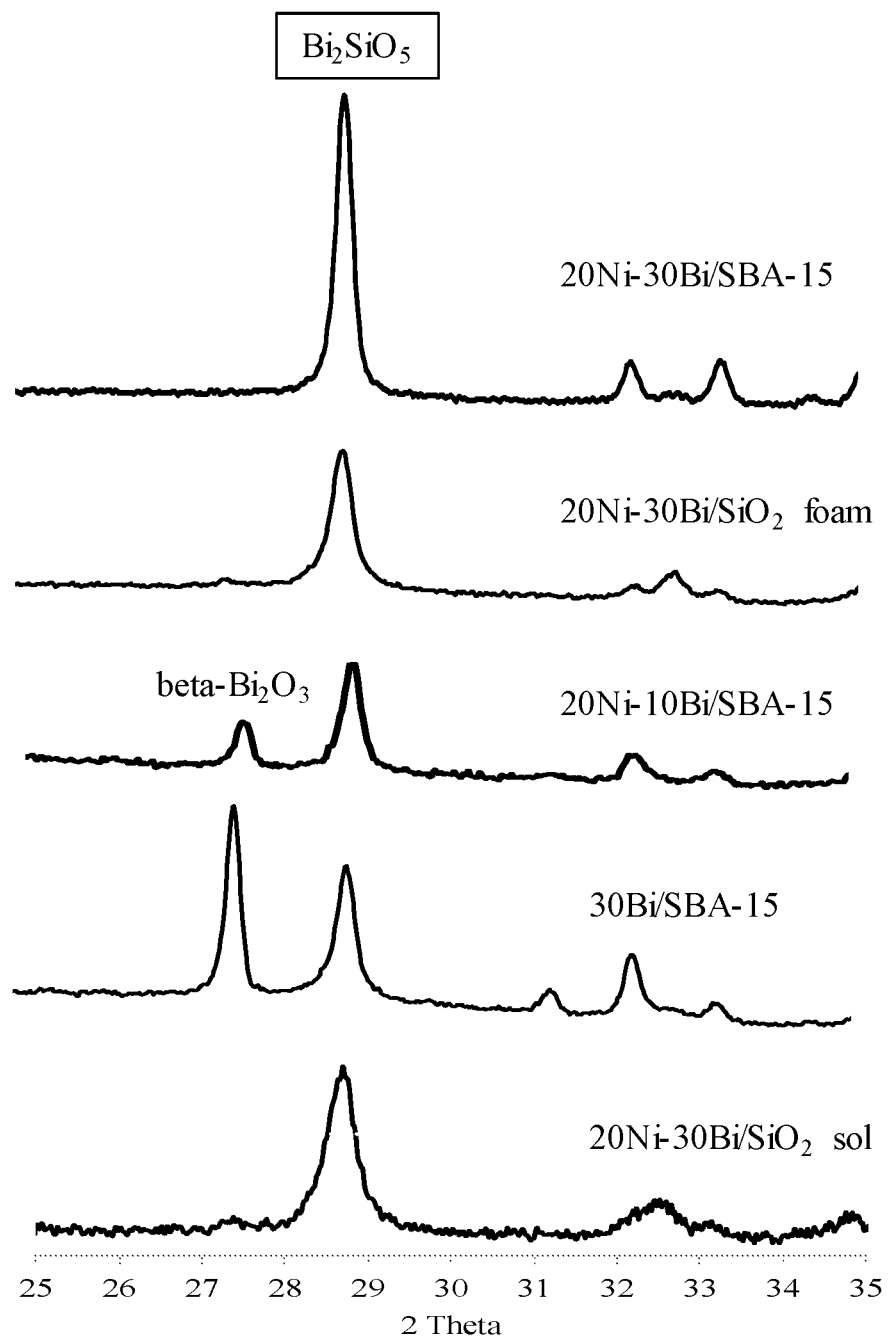

MESOPOROUS COMPOSITE CATALYSTS CONTAINING BISMUTH SILICATE AND TRANSITION METAL OXIDE

BACKGROUND OF THE INVENTION

Technical Field

The present disclosure relates to mesoporous silica supported bismuth silicate and transition metal oxide-based catalysts and their use for oxidative dehydrogenation of alkanes and/or alkenes to corresponding dienes.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Recently there has been a growing global demand for butadiene, which is an important raw material for manufacturing synthetic rubber. One of "on-purpose" butadiene production technologies is oxidative dehydrogenation of n-butane using metal oxide hybridized mesoporous materials. The catalytic conversion of low-value feedstocks such as n-butane over metal oxide hybridized mesoporous materials is of great interest to the growing petrochemical industry, especially to produce synthetic rubbers.

Zhang et al. [L. Zhang, W. Wang, S. Sun, J. Xu, M. Shang, J. Ren, Appl. Catal. B: Environ. 100 (2010) 97-101, incorporated herein by reference in its entirety] report hybrid $Bi_2SiO_5$ mesoporous microspheres for decomposing dyes including tetra-ethylated rhodamine (RhB) and phenol under light irradiation. The hybrid meso-structured photocatalyst was prepared using the periodic mesoporous organo-silicas (PMO) framework and a bismuth salt (e.g. bismuth nitrate) via a post synthetic modification approach. The hybrid $Bi_2SiO_5$ photocatalyst were characterized by X-ray diffraction (XRD), transmission electron microscopy (TEM), and $N_2$ adsorption-desorption isotherms.

Lu et al. [J. Lu, X. Wang, Y. Wu, Y. Xu, Mater. Lett. 74 (2012) 200-202, incorporated herein by reference in its entirety] report the synthesis of pure $Bi_2SiO_5$ powder by molten salt method in $NaCl$—$Na_2SO_4$ flux using $Bi_2O_3$ and $SiO_2$ as raw materials. The authors conclude that calcination temperature plays a crucial role in the production of $Bi_2SiO_5$ powder. The authors further indicate that the synthesis of $Bi_2SiO_5$ powder by molten salt method undergoes a "dissolution-precipitation mechanism".

Guo et al. [H. W. Guo, X. F. Wang, D. N. Gao, Mater. Lett. 67 (2012) 280-282, incorporated herein by reference in its entirety] report a process for preparing pure $Bi_2SiO_5$ crystals via a melt-cooling process using $Bi_2O_3$ and $SiO_2$ as starting materials. The $Bi_2SiO_5$ crystal samples were characterized by thermo gravimetric (TG), differential scanning calorimeter (DSC), field-emission scanning electron microscopy (FESEM), and X-ray diffraction (XRD). XRD and SEM images demonstrate that highly ordered lamellar $Bi_2SiO_5$ crystals with coarse grains are produced via heating at 805.3° C. for about 2 hours.

Hussain et al. [M. Hussain, S. S. Batool, Z. Imran, M. Ahmad, K. Rasoo, M. A. Rafiq, M. M. Hasan, Sens. Actuators B 192 (2014) 429-438, incorporated herein by reference in its entirety] report nanofibers of silica, bismuth doped silica, and bismuth silicate prepared via electrospinning method. The gas sensing (e.g. oxygen gas sensing) and transport properties of the $SiO_2$ nanofibers, bismuth doped $SiO_2$ nanofibers, and bismuth silicate ($Bi_4(SiO_4)_3$) nanofibers were investigated.

Gu et al. [W. Gu, F. Teng, Z. Liu, Z. Liu, J. Yang, Y. Teng, J. Photochem. Photobiol. A 353 (2018) 395-400, incorporated herein by reference in its entirety] report the synthesis $Bi_2SiO_5$ and $Bi_{12}SiO_{20}$. The authors study photocatalytic properties of layered $Bi_2SiO_5$ and body centered $Bi_{12}SiO_{20}$ under visible light (>420 nm) and UV light irradiations. Specifically, $Bi_{12}SiO_{20}$ efficiently degrades rhodamine B (RhB) under visible light, while $Bi_2SiO_5$ demonstrates greater photoactivity than $Bi_{12}SiO_{20}$ under UV light.

Lua et al. [H. Lu, Q. Hao, T. Chena, L. Zhang, D. Chen, C. Ma, W. Yao, Y. Zhu, Appl. Catal. B: Environ. 237 (2018) 59-67, incorporated herein by reference in its entirety] report a high-performance $Bi_2O_3/Bi_2SiO_5$ p-n heterojunction photocatalyst synthesized via phase transition of $Bi_2O_3$. The photocatalyst was prepared via a one-step synthesis using a bismuth salt (e.g. $Bi(NO_3)_3$) and nano-$SiO_2$ as precursors. The photocatalyst samples were examined using various analytical tools including X-ray powder diffraction (XRD), scanning electron microscopy (SEM), energy-dispersive spectrometry (EDS), transmission electron microscopy (TEM), X-ray photoelectron spectroscopy (XPS), and UV-vis diffuse reflectance spectroscopy (DRS). The $Bi_2O_3/Bi_2SiO_5$ heterojunction photocatalysts are capable of degrading organic pollutants under sunlight. The authors conclude that the photocatalytic activity is attributable to large surface area, contact angle, $\beta$-$Bi_2O_3$ formation, and p-n heterojunctions of the catalyst.

In all the above cases, $Bi_2SiO_5$ materials are only utilized for electrical and photocatalytic applications. Catalysts containing bismuth silicate and additional transition metals supported on mesoporous silica and their application for the conversion of hydrocarbons to olefins and/or diolefins have not been disclosed or studied.

In view of the forgoing, one objective of the present disclosure is to provide composite catalysts containing bismuth silicate(s) and transition metal oxide(s) impregnated on a mesoporous silica support such as SBA-15, mesoporous silica foam, and silica sol. Another objective of the present disclosure is to provide a method of making these composite catalysts. A further objective of the present disclosure is to provide a process of oxidatively dehydrogenating alkanes and/or alkenes to corresponding dienes utilizing these composite catalysts which leads to enhanced feed conversion and diene selectivity.

BRIEF SUMMARY OF THE INVENTION

According to a first aspect, the present disclosure relates to a composite catalyst including a mesoporous silica support which is at least one selected from the group consisting of SBA-15, mesoporous silica foam, and silica sol, and a catalytic material comprising a bismuth silicate and a transition metal oxide impregnated on the mesoporous silica support, wherein the composite catalyst is devoid of molybdenum.

In one embodiment, the bismuth silicate is $Bi_2SiO_5$.

In one embodiment, the transition metal oxide is at least one selected from the group consisting of nickel(II) oxide, iron(II) oxide, and cobalt(II) oxide.

In one embodiment, the transition metal oxide is nickel (II) oxide.

In one embodiment, the composite catalyst comprises 5-40 wt % of bismuth atoms and 10-30 wt % of transition metal atoms, each relative to a weight of the mesoporous silica support.

In one embodiment, the catalytic material further comprises bismuth oxide.

According to a second aspect, the present disclosure relates to a method of preparing the composite catalyst of the first aspect. The method involves (i) mixing a transition metal salt and a bismuth salt in a solvent to form a first mixture, (ii) mixing the first mixture and the mesoporous silica support to form a second mixture, (iii) drying the second mixture to form a dried mass, and (iv) calcining the dried mass in air, thereby producing the composite catalyst.

In one embodiment, the transition metal oxide is nickel (II) oxide, and the transition metal salt is nickel(II) nitrate.

In one embodiment, the bismuth salt is bismuth(III) nitrate.

In one embodiment, the solvent includes water.

In one embodiment, the second mixture is dried at a temperature ranging from 50° C. to 200° C.

In one embodiment, the dried mass is calcined in air at a temperature ranging from 300° C. to 700° C.

According to a third aspect, the present disclosure relates to a process of oxidatively dehydrogenating an alkane and/or an alkene to a corresponding diene. The process involves flowing a feed mixture comprising the alkane and/or the alkene, and an oxidant through a reactor loaded with the composite catalyst of the present disclosure, in one or more of its embodiments, thereby forming the corresponding diene.

In one embodiment, the alkane is n-butane, the alkene is a butene, and the corresponding diene is butadiene.

In one embodiment, a molar ratio of the oxidant to a total amount of the alkane and/or the alkene ranges from 0.1:1 to 8:1.

In one embodiment, the flowing is performed at a temperature ranging from 250° C. to 700° C.

In one embodiment, the oxidant is $O_2$.

In one embodiment, the feed mixture comprises n-butane, and the process has a butadiene yield of 10-20 wt % relative to a weight of n-butane.

In one embodiment, the feed mixture comprises n-butane, and the process further forms butenes with a molar ratio of butadiene to butenes ranging from 1:1 to 3:1.

In one embodiment, the feed mixture comprises 2-butene, and the process has a butadiene yield of 30-80 wt % relative to a weight of 2-butene.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWING

A more complete appreciation of the disclosure and many of the attendant advantages thereof will be readily obtained as the same becomes better understood by reference to the following detailed description when considered in connection with the accompanying drawings, wherein:

FIG. 1 is an overlay of X-ray diffraction (XRD) patterns of different catalysts each including a silica support and a catalytic material of bismuth silicate and optionally nickel oxide impregnated on the respective silica support (see Examples 2-6 for composition details).

DETAILED DESCRIPTION OF THE EMBODIMENTS

Embodiments of the present disclosure will now be described more fully hereinafter with reference to the accompanying drawings, in which some, but not all embodiments of the disclosure are shown.

The present disclosure may be better understood with reference to the following definitions. As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the words "substantially similar", "approximately", or "about" may be used when describing magnitude and/or position to indicate that the value and/or position described is within a reasonable range of values and/or positions. For example, a numeric value may have a value that is ±1% of the stated value (or range of values), ±2% of the stated value (or range of values), ±5% of the stated value (or range of values), ±10% of the stated value (or range of values), ±15% of the stated value (or range of values), or ±20% of the stated value (or range of values).

As used herein, the terms "compound" or "salt" refers to a chemical entity, whether in a solid, liquid or gaseous phase, and whether in a crude mixture or purified and isolated.

The present disclosure includes all hydration states of a given compound or formula, unless otherwise noted. For example, $Ni(NO_3)_2$ includes anhydrous $Ni(NO_3)_2$, $Ni(NO_3)_2 \cdot 6H_2O$, and any other hydrated forms or mixtures. $Bi(NO_3)_3$ includes both anhydrous $Bi(NO_3)_3$ and $Bi(NO_3)_3 5H_2O$.

The present disclosure further includes all isotopes of atoms occurring in the present catalysts. Isotopes include those atoms having the same atomic number but different mass numbers. By way of general example, and without limitation, isotopes of hydrogen include deuterium and tritium, isotopes of carbon include $^{13}C$ and $^{14}C$, isotopes of oxygen include $^{16}O$, $^{17}O$ and $^{18}O$, and isotopes of nickel include $^{58}Ni$, $^{60}Ni$, $^{61}Ni$, and $^{64}Ni$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a composite catalyst including a mesoporous silica support which is at least one selected from the group consisting of mesoporous silica such as SBA-15, mesoporous silica foam, and silica sol, and a catalytic material containing a bismuth silicate and a transition metal oxide impregnated on the mesoporous silica support.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components.

As used herein, a support material refers to a material, usually a solid with a surface area, to which a catalyst is affixed. A "mesoporous support" refers to a porous support material with largest pore diameters ranging from about 2-50 nm, preferably 3-45 nm, preferably 4-40 nm, preferably 5-25 nm. Typical support materials include various kinds of carbon, alumina, and silica. In a preferred embodiment, the catalyst of the present disclosure comprises a mesoporous silica support. In one or more embodiments, the mesoporous silica support is at least one selected from the group consisting of SBA-15, mesoporous silica foam, and silica sol. In a preferred embodiment, the mesoporous silica support is SBA-15.

The Brunauer-Emmet-Teller (BET) theory (S. Brunauer, P. H. Emmett, E. Teller, *J. Am. Chem. Soc.* 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross-sectional area. In most embodiments, pore volume and BET surface area are measured by gas adsorption analysis, preferably $N_2$ adsorption analysis.

In one embodiment, the mesoporous silica support has a pore volume of 0.2-3 cm$^3$/g, 0.5-2.5 cm$^3$/g, 0.8-2.0 cm$^3$/g, or 1.0-1.5 cm$^3$/g. In one embodiment, the mesoporous silica support has a BET surface area of 200-1,000 m$^2$/g, 300-900 m$^2$/g, 400-800 m$^2$/g, or 500-700 m$^2$/g.

In one embodiment, the mesoporous silica support has pore channels that are regularly arranged. For example, the mesoporous silica support is in the form of a honeycomb-like structure having pore channels parallel or substantially parallel to each other within a two-dimensional hexagon (e.g. SBA-15). Alternatively, other mesoporous silica structures of the SBA series such as SBA-11 having a cubic structure, SBA-12 having a three-dimensional hexagonal structure, and SBA-16 having a cubic in cage-like structure may be used as the mesoporous silica support. In one embodiment, the mesoporous silica support is in the form of SBA-15, and the mesoporous silica support has a pore volume of 0.2-1.5 cm$^3$/g, 0.4-1.2 cm$^3$/g, or 0.5-1.0 cm$^3$/g and a BET surface area of 200-800 m$^2$/g, 400-700 m$^2$/g, or 500-600 m$^2$/g.

As defined herein, a silica foam is a foam silicate that has interconnected cells joined at a nexus, with varying properties depending on the nature of the surfactant used and the method of synthesis. A surfactant templated mesoporous silica foam has porosity resulting from the presence of silicate struts that define cage-like cellular pores connected by windows. In one embodiment, the mesoporous silica support described herein is a mesoporous silica foam. In certain embodiments, the mesoporous silica foam is amorphous having a non-ordered structure. This non-ordered structure may be random and thus different than the aforementioned mesoporous silica structures and SBA silica structures. Specifically, when a mesoporous silica foam is used, the mesoporous silica support has a pore volume of 1.5-3 cm$^3$/g, 2.0-2.7 cm$^3$/g, or 2.2-2.5 cm$^3$/g, and a BET surface area of 400-1,000 m$^2$/g, 500-800 m$^2$/g, or 600-700 m$^2$/g.

The sol materials may be prepared via a wet sol forming process where an oxide network formed resulting to nano-sized $SiO_2$ precursor through hydrolysis and polycondensation reactions of molecular precursor(s) (e.g. tetraethyl orthosilicate (TEOS), tetramethoxysilane (TMOS)) in a liquid form (water solution). The wet sol forming process may be considered as "the unaggregated to wet gel". The wet sol is used as a dry sol after being dried at a temperature below 200° C. Alternatively, the dry sol material may be directly prepared via a dry sol forming process from tetrachlorosilane burning as a fumed silica. The sol materials obtained may be referred to as a "gel" if an additional calcination treatment at a temperature of 300-700° C. is carried out. The silica sol used herein may be commercially available or prepared in-house according to methods known to one of ordinary skill in the art. For example, a silica sol may be formed by mixing the molecular precursor (e.g. TEOS, TMOS) optionally with additives (e.g. such as urea, ammonium hydroxide, sodium hydroxide) to produce a mixture, and aging and drying the mixture at a temperature of 70-150° C., 80-130° C., or about 120° C. for 0.5-6 hours, 1-5 hours, or about 3 hours. In one embodiment, the silica sol contributes to the catalyst mesoporosity in the regularly structured form of silica sol as the mesoporous silica support which has a pore volume of 0.4-2.0 cm$^3$/g, 0.8-1.5 cm$^3$/g, or 0.9-1.1 cm$^3$/g, and a BET surface area of 75-300 m$^2$/g, 100-200 m$^2$/g, or 130-150 m$^2$/g. Alternatively, the silica sol contributes to the catalyst mesoporosity in the irregularly structured form of silica sol as the mesoporous silica support which has a pore volume of 0.5-2.2 cm$^3$/g, 0.9-1.6 cm$^3$/g, or 1.0-1.2 cm$^3$/g, and a BET surface area of 100-450 m$^2$/g, 150-300 m$^2$/g, or 200-250 m$^2$/g.

Mesoporous composites are key materials that can be used for industrial catalytic conversion, especially for converting n-butane/butenes to 1,3-butadiene. Bismuth silicate ($Bi_2SiO_5$) is a newly discovered compound in the Aurivillius family initially reported in 1996 [J. Park, B. G. Kim, S. Mori, T. Oguchi, J. Solid State Chem. 235 (2016) 68-75; and D. Liu, W. Yao, J. Wang, Y. Liu, M. Zhang, Y. Zhu, Appl. Catal. B Environ. 172 (2015) 100-107, each incorporated herein by reference in their entirety]. It has been recognized that $Bi_2SiO_5$ has a two-dimensional structure with alternately stacked $(Bi_2O_2)^{2+}$ and $(SiO_3)^{2-}$ layers [Y. Wu, M. Li, J. Yuan, X. Wang, J. Mater. Sci. (2017) 1-5; and Y. Kim, J. Kim, A. Fujiwara, H. Taniguchi, S. Kim, H. Tanaka, K. Sugimoto, K. Kato, M. Itoh, H. Hosono, IUCrJ 1 (2014) 160-164, each incorporated herein by reference in their entirety]. The advantages of using bismuth silicate include its non-toxicity, chemical stability, and excellent photocatalytic activity [D. Liu, J. Wang, M. Zhang, Y. Liu, Y. Zhu, Nanoscale 6 (2014) 15222-15227; L. Zhang, W. Wang, S. Sun, J. Xu, M. Shang, J. Ren, Appl. Catal. B Environ. 100 (2010) 97-101; and R. Chen, J. Bi, L. Wu, W. Wang, Z. Li, X. Fu, Inorg. Chem. 48 (2009) 9072-9076, each incorporated herein by reference in their entirety]. However, $Bi_2SiO_5$ has only been utilized in the field of photocatalysis.

The bismuth silicate present in the catalytic material may be at least one selected from the group consisting of $Bi_2SiO_5$, $Bi_2O_9Si_3$, $Bi_4Si_3O_{12}$, and $Bi_{12}SiO_{20}$. In a preferred embodiment, the bismuth silicate is $Bi_2SiO_5$. Bismuth atoms of the bismuth silicate may be present in an amount of 5-40 wt %, preferably 10-36 wt %, more preferably 20-31 wt %, or about 30 wt % relative to a weight of the mesoporous silica support.

The transition metal oxide present in the catalytic material may be at least one oxide of a transition metal selected from the group consisting of Sc, Ti, V, Cr, Mn, Fe, Co, Ni, Cu, Y, Zr, Nb, Tc, Ru, Rh, Pd, Ag, Hf, Ta, W, Re, Os, Ir, Pt, Au, Rf, Db, Sg, Bh, Hs, Mt, Ds, Rg, and Cn. In one or more embodiments, the transition metal oxide is an oxide of Ni, Fe, and/or Co. In a preferred embodiment, the transition metal oxide is at least one selected from the group consisting of nickel(II) oxide, iron(II) oxide, and cobalt(II) oxide. Most preferably, the transition metal oxide is nickel(II) oxide. The transition metal atoms of the transition metal oxide may be present in an amount of 2-30 wt %, preferably 5-26 wt %, more preferably 10-21 wt %, or about 20 wt % relative to a weight of the mesoporous silica support.

The amounts of transition metal and bismuth atoms in the composite catalyst may vary depending upon the properties sought (e.g. catalytic activities, surface property of the mesoporous silica support) as well as the dispersibility of the transition metal oxide and bismuth silicate in the mesoporous silica support. In some embodiments, bismuth silicate (e.g. $Bi_2SiO_5$) is present in the composite catalyst in an amount of 5.5-50 wt %, 11-42 wt %, or 22-35 wt % relative to a weight of the mesoporous silica support. In some embodiments, the transition metal oxide (e.g. nickel(II) oxide) is present in the catalyst at an amount of 2.5-40 wt %, 6-35 wt %, or 12-28 wt % relative to a weight of the mesoporous silica support. In a related embodiment, a weight ratio of the transition metal atoms of the transition metal oxide to bismuth atoms of bismuth silicate is in a range of 1:20 to 6:1, preferably f 1:10 to 4:1, preferably 1:5 to 2:1, preferably 1:2 to 3:2, preferably 2:3 to 1:1.

When the transition metal oxide present in the composite catalyst is a nickel oxide, the nickel oxide may have a NiO crystalline bunsenite morphology, which has an isometric or cubic crystal system. The crystalline NiO may have a structure within the Fm3m space group, and the structure may be part of the hexoctahedral crystal class. In another embodiment, the nickel oxide may be amorphous, or have different crystal morphology. In certain embodiments, the nickel oxide comprises less than 100 wt % NiO, and further comprises Ni(0) and/or Ni(III) (e.g. $Ni_2O_3$). Preferably the nickel oxide comprises at least 90 wt % NiO, preferably at least 95 wt % NiO, more preferably at least 99 wt % NiO, even more preferably 99.5 wt % NiO, or about 100 wt % NiO, relative to a total weight of the nickel oxide.

The bismuth species used for formation of the $Bi_2SiO_5$ phase can also lead to generation of a bismuth oxide ($Bi_2O_3$) phase. Bismuth oxide has four crystalline forms including α, β, γ, and δ phases, corresponding to monoclinic, tetragonal, body-centered cubic, and face-centered cubic forms, respectively. β-$Bi_2O_3$ is a metastable state and is unstable at ambient temperature. Thus, practical application of single-component α-$Bi_2O_3$ or β-$Bi_2O_3$ for catalysis has been greatly limited. However, Jermy et al. [B. R. Jermy, S. Asaoka, S. Al-Khattaf, Catal. Sci. Technol. 5 (2015) 4622-4635, incorporated herein by reference in its entirety] reported that the mixed phases of bismuth oxide could promote catalytic performance. Co-existing $Bi_2O_3$ and $Bi_2SiO_5$ species may act as a carrier that enables an accelerated migration of active element and thereby improves the activity, selectivity, and stability of the catalyst.

In one or more embodiments, the catalytic material of the composite catalyst disclosed herein in any of its embodiments further comprises bismuth oxide ($Bi_2O_3$). The bismuth oxide may be comprised of a plurality of different crystallographic phases. Bismuth oxide has five crystallographic polymorphs. The room temperature phase, α-$Bi_2O_3$ is stable and has a monoclinic crystal structure having layers of oxygen atoms with layers of bismuth atoms between them. There are three high temperature phases, a tetragonal β-phase, a body-centered cubic γ-phase, a cubic δ-$Bi_2O_3$ phase and a ε-phase. In the present disclosure, the bismuth oxide may refer to $Bi_2O_3$ having an a polymorph, a β polymorph, a γ polymorph, a δ polymorph, a c polymorph, or mixtures thereof. In another embodiment, the bismuth oxide may be amorphous, or have different crystal morphology. In a preferred embodiment, the bismuth oxide present in the composite catalyst has a α polymorph and/or a β polymorph. Most preferably, the bismuth oxide has a β polymorph. In one embodiment, when bismuth oxide is present in the composite catalyst, a weight ratio of bismuth silicate to bismuth oxide is in a range of 1:10 to 10:1, 1:8 to 8:1, 1:6 to 6:1, 1:4 to 4:1, or 1:2 to 2:1.

X-ray diffraction (XRD) patterns of the bismuth oxide may provide information including, which crystalline phases are present (peak locations), relative amounts of each phase (integrated area under respective peaks), and crystallite size (peak width at half max). The different bismuth oxide phases that can be present in the mesoporous silica support may depend on the synthesis method, the bismuth precursor, solvent, calcination temperature, bismuth oxide loading, the mesoporous silica support, etc. As shown in FIG. 1, the catalytic material of the composite catalyst contains both bismuth silicate and β-bismuth oxide when the weight ratio of the transition metal atoms (e.g. nickel) to bismuth atoms is greater than 1:1 (e.g. 1.4:1, 2:1). However, when a weight ratio of the transition metal atoms (e.g. nickel) to bismuth atoms is less than 1:1 (e.g. about 2:3), the catalytic material of the composite catalyst is devoid of β-bismuth oxide.

In one embodiment, the composite catalyst of the present disclosure contains substantially no molybdenum, for instance, less than 0.1 wt % of molybdenum, preferably less than 0.05 wt %, more preferably less than 0.01 wt % of molybdenum, relative to a weight of the mesoporous silica support. In at least one embodiment, the composite catalyst is devoid of molybdenum.

In a preferred embodiment, the composite catalyst of the present disclosure comprises a catalytic material comprising bismuth silicate, transition metal oxide, and optional bismuth oxide impregnated on the mesoporous silica support. As used herein, "impregnated" or "disposed on" describes being completely or partially filled throughout, saturated, permeated, and/or infused. The catalytic material may be affixed on one or more surfaces of the mesoporous silica support. For example, the catalytic material may be affixed on an outer surface of the mesoporous silica support and/or within pore spaces of the mesoporous silica support. The catalytic material may be affixed to the mesoporous silica support in any reasonable manner, such as physisorption, chemisorption, or combinations thereof. In one embodiment, greater than 10% of the surface area (i.e. outer surface and pore spaces) of the mesoporous silica support is covered by the catalytic material. Preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, or preferably greater than 99% of the surface area of the mesoporous silica support is covered by the catalytic material.

In one embodiment, the mesoporous silica support is covered with a thin layer of the catalyst material having an average thickness of 0.5-20 nm, 1-15 nm, 2-10 nm, 2.5-8 nm, or 3-6 nm. At high enough loadings, nanocrystals or nanoparticles of the catalytic material (e.g. bismuth silicate, transition metal oxide, optional bismuth oxide, and mixtures thereof) having an average particle size of 1-50 nm, preferably 2-40 nm, preferably 3-30 nm, preferably 4-20 nm may be present on the surface of the mesoporous silica support. In one or more embodiments, the bismuth silicate and transition metal oxide (e.g. nickel oxide) are homogeneously distributed throughout the mesoporous silica support. In a preferred embodiment, the transition metal oxide (e.g. nickel oxide) is dispersed on the bismuth silicate. Alternatively, the transition metal oxide (e.g. nickel oxide) may form localized clusters amongst the bismuth silicate. The distinct bismuth and transition metal species and their distributions on the mesoporous silica support may be identified by techniques including, but not limited to, UV-vis spectroscopy, XRD, Raman spectroscopy, AFM (atomic force microscope), TEM (transmission electron microscopy), and EPR (electron paramagnetic resonance).

The bismuth silicate is preferably dispersed on the mesoporous silica support. In an embodiment where the bismuth silicate is well dispersed (i.e., not agglomerated), the bismuth silicate may be evenly dispersed (i.e., a distance between a bismuth silicate species and all its neighbors is the same or substantially the same) or randomly dispersed (i.e., the distance between a bismuth silicate species and all its neighbors are different). The distance can be said to be substantially the same when the shortest distance is at least 80%, at least 85%, at least 90%, or at least 95% of the average distance and the longest distance is not more than 120%, not more than 110%, or not more than 105% of the average distance. Alternatively, the bismuth silicate is agglomerated. Energy-dispersive X-ray spectroscopy, X-ray microanalysis, elemental mapping, transmission electron microscopy (TEM), scanning electron microscopy (SEM), and scanning transmission electron microscopy may be useful techniques for observing the dispersion of the bismuth silicate on the mesoporous silica support.

In one or more embodiments, the composite catalyst disclosed herein in any of its embodiments has a BET surface area of 50-1,000 m$^2$/g, preferably 80-800 m$^2$/g, preferably 100-700 m$^2$/g. In one related embodiment, the composite catalyst has an average pore diameter of 2-30 nm, preferably 3-20 nm, preferably 4-18 nm, preferably 5-16 nm, preferably 8-12 nm. In another related embodiment, the composite catalyst has a pore volume of 0.1-3 cm$^3$/g, preferably 0.2-2 cm$^3$/g, preferably 0.3-1.5 cm$^3$/g, preferably 0.5-1 cm$^3$/g.

According to a second aspect, the present disclosure relates to a method of preparing the composite catalyst of the first aspect, in one or more of its embodiments. The method involves the steps of (i) mixing a transition metal salt and a bismuth salt in a solvent to form a first mixture, (ii) mixing the first mixture and the mesoporous silica support to form a second mixture, (iii) drying the second mixture to form a dried mass, and (iv) calcining the dried mass in air, thereby producing the composite catalyst.

Two main methods are typically used to prepare supported catalysts. In the impregnation method, the solid support or a suspension of the solid support is treated with a solution of a pre-catalyst (for instance a metal salt or metal coordination complex), and the resulting material is then activated under conditions that will convert the pre-catalyst to a more active state, such as metal oxides of the metal or the metal itself. Alternatively, supported catalysts can be prepared from a homogenous solution by co-precipitation. In terms of the present disclosure, it is envisaged that the catalyst may be formed by an impregnation method or a co-precipitation method, preferably by an impregnation method. The mesoporous silica support used herein is preferably thermally stable and withstands processes required for pre-catalyst activation. For example, pre-catalysts may be activated by exposure to a stream of air (oxygen) or hydrogen at high temperatures, additionally pre-catalysts may be further activated and/or reactivated by oxidation-reduction cycles, again at high temperatures.

In one step of the method, a transition metal salt and a bismuth salt are mixed with a solvent to form a first mixture. In one embodiment, the bismuth salt may be a bismuth(III) salt. Exemplary bismuth salts include, but are not limited to, bismuth(III) nitrate, bismuth(III) sulfate, bismuth(III) acetate, bismuth(III) chloride, bismuth(III) bromide, bismuth(III) iodide, bismuth(III) phosphate, bismuth hydroxide, bismuth(III) citrate, bismuth(III) oxynitrate, bismuth (III) oxychloride, and the like. In one embodiment, more than one type of bismuth(III) salt may be used. Preferably, the bismuth salt is bismuth(III) nitrate. In one embodiment, the transition metal oxide is a nickel oxide, preferably nickel(II) oxide, and the transition metal salt is a nickel salt, preferably a nickel(II) salt, though in an alternative embodiment, nickel having a different oxidation state, such as +3, may be used. Exemplary nickel salts include, but are not limited to, nickel(II) nitrate, nickel(II) sulfate, ammonium nickel(II) sulfate, nickel(II) acetate, nickel(II) chloride, nickel(II) bromide, nickel(II) iodide, nickel(II) perchlorate, and the like. In one embodiment, more than one type of nickel(II) salt may be used. Preferably, the nickel salt is nickel(II) nitrate. In a preferred embodiment, the solvent is a polar protic solvent. Exemplary polar protic solvents include, and are not limited to, water, methanol, ethanol, iso-propanol, and n-butanol. Preferably, the solvent is water.

In a most preferred embodiment, the first mixture contains water as the solvent, bismuth(III) nitrate as the bismuth salt, and nickel(II) nitrate as the transition metal salt. The nickel salt may be present in the first mixture in an amount of 8-80 mM, preferably 10-70 mM, preferably 15-60 mM relative to a total volume of the first mixture. The bismuth salt may be present in the first mixture in an amount of 4-40 mM, preferably 8-35 mM, preferably 10-30 mM relative to a total volume of the first mixture. In a preferred embodiment, a weight ratio of nickel to bismuth atoms in the first mixture is in a range of 1:20 to 6:1, preferably 1:10 to 4:1, preferably 1:5 to 2:1, preferably 1:2 to 3:2, preferably 2:3 to 1:1.

In another step of the method, the mesoporous silica support is mixed with the first mixture comprising the bismuth salt and the transition metal salt to form a second mixture. In some embodiments, a weight ratio of bismuth atoms to the mesoporous silica support present in the second mixture ranges from 1:2 to 1:6, preferably 1:3 to 1:5, preferably 3:10 to 1:4. In some embodiments, a weight ratio of transition metal atoms (e.g. nickel atoms) to the mesoporous silica support present in the second mixture ranges from 1:2 to 1:10, preferably 1:3 to 1:8, preferably 1:4 to 1:6. In a related embodiment, a weight ratio of the mesoporous silica support to the transition metal salt (e.g. nickel salt) ranges from 1:3 to 3:1, preferably 1:2 to 2:1, preferably 2:3 to 3:2. A weight ratio of the mesoporous silica support to the bismuth salt may range from 1:2 to 4:1, preferably 2:3 to 2:1, preferably 1:1 to 4:3.

Typically a main method of disposing catalytic species on a support material is wet impregnation conducted in a mixture where the bismuth silicate and transition metal oxide precursors are soluble or partially soluble. In one embodiment, the impregnation method is performed by contacting the mesoporous silica support with a certain volume of the first mixture containing the dissolved or partially dissolved bismuth and transition metal salts. In one embodiment, the mesoporous silica support may be initially dried and/or calcined to remove volatile impurities. The initial drying may be performed at a temperature of 200-400° C., 250-350° C., or 300-320° C. for a period of up to 6 hours, preferably up to 3 hours, or about 1 hour. The initial calcining may be performed at a temperature of 450-800° C., 500-700° C., or 550-650° C. for a period of up to 12 hours, preferably up to 6 hours, or about 2 hours.

In a preferred embodiment, mixing the mesoporous silica support with the first mixture is performed at a temperature of 10-50° C., preferably 20-40° C., preferably 25-30° C. for a period of 4-24 hours, 8-20 hours, or 12-16 hours and optionally with stirring and/or ultrasonication to achieve a homogeneous mixture.

The method also involves the step of drying the second mixture to form a dried mass. Preferably this step involves removing the solvent (e.g. water) from the second mixture and facilitating deposition of bismuth and transition metal species on the mesoporous silica support. In one embodiment, this step involves heating the second mixture to evaporate the solvent. In one or more embodiments, the second mixture is dried at 50-100° C., 70-90° C., or about 80° C. in order to remove the solvent (e.g. water). In certain embodiments, the second mixture may be further heated at 100-150° C., 110-130° C., or about 120° C. for 1-6 hours, 2-4 hours, or about 3 hours to form a dried mass. In other embodiments, the second mixture may be subjected to a vacuum, or a rotary evaporator. In another embodiment, the second mixture may be heated in an oven, or left at room temperature.

The dried mass may be calcined in air within a furnace or oven at a temperature of 300-700° C., 350-600° C., or 400-500° C., though in some embodiments, the dried mass may be heated at a temperature of lower than 300° C. or higher than 700° C. In some embodiments, the dried mass may not be heated in air, but oxygen-enriched air, an inert gas, or a vacuum. Preferably the dried mass is placed in an oven at room temperature or 20-50° C., and then the temperature is increased to a first target calcining temperature of 300-450° C., 325-400° C., or about 350° C. at a rate of 5-15° C./min, preferably 8-12° C./min, or about 10° C./min. The dried mass may be maintained at the first target calcining temperature for 0.1-3 hours, 0.5-2 hours, or about 1 hour. Preferably the temperature of the oven is further increased to a second target calcining temperature of 450-700° C., 500-650° C., or about 590° C. at a rate of 10-20° C./min, 12-18° C./min, or about 15° C./min. The dried mass may be maintained at the second target calcining temperature for 0.5-6 hours, 1-4 hours, or about 2 hours. Calcining the dried mass produces the composite catalyst.

It is equally envisaged that the method may be adapted to other means of dispersing and impregnating the bismuth silicate and transition metal oxide on the mesoporous silica support. Exemplary other means include, but are not limited to, isomorphous substitution, enforced impregnation, vapor-fed flame synthesis, flame spray pyrolysis, sputter deposition, atomic layer deposition, and chemical vapor deposition.

According to a third aspect, the present disclosure relates to a process of oxidatively dehydrogenating an alkane and/or an alkene to a corresponding diene. The process involves flowing a feed mixture containing the alkane and/or the alkene, and an oxidant through a reactor loaded with the composite catalyst of the present disclosure, in one or more of its embodiments, thereby forming the corresponding diene.

As used herein, dehydrogenation refers to a chemical reaction that involves the removal of hydrogen from a molecule. It is the reverse process of hydrogenation. The dehydrogenation reaction may be conducted on both industrial and laboratory scales. Essentially, dehydrogenation processes convert saturated compounds/functionalities to unsaturated compounds/functionalities and hydrogen. Dehydrogenation processes are used extensively in fine chemicals, oleochemicals, petrochemicals and detergents industries. The catalytic dehydrogenation of alkanes and/or alkenes is more selective to particular degrees of dehydrogenation but the reaction characteristics pose inherent difficulties and impose certain technical constraints. For example, thermal dehydrogenation is strongly endothermic and often requires operation at both high temperature and high alkane partial pressure. The oxidative dehydrogenation (ODH) of an alkane or an alkene, which couples the endothermic dehydrogenation of the alkane and/or the alkene with the strongly exothermic oxidation of hydrogen avoids the need for excess internal heat input and consumes hydrogen.

As defined herein, a butene refers to 1-butene, (Z)-but-2-ene, (E)-but-2-ene, or mixtures thereof "Butenes" used herein refers to an aggregate of all butenes generated during the process of oxidative dehydrogenation. In a preferred embodiment, the alkane is n-butane, the alkene is a butene, and the corresponding diene is butadiene. In some embodiments, the feed mixture contains n-butane, and the process disclosed herein further forms butenes.

The general nature of the alkane and alkene substrates is not viewed as particularly limiting to the oxidative dehydrogenation described herein. It is equally envisaged that the present disclosure may be adapted to oxidatively dehydrogenate other alkanes in addition to, or in lieu of n-butane to form corresponding alkenes. As used herein, "alkane" unless otherwise specified refers to both branched and straight chain saturated aliphatic primary, secondary, and/or tertiary hydrocarbons of typically $C_2$ to $C_{12}$, $C_3$ to $C_{10}$, $C_4$ to $C_8$, or $C_5$ to $C_6$. Other exemplary alkanes include, but are not limited to, straight or branched alkanes of $C_1$ to $C_{10}$ such as ethane ($C_2H_6$), propane ($C_3H_8$), and isobutane, and the corresponding alkene such as ethylene, propylene, and isobutylene (2-methylpropene). Cycloalkanes, which are optionally substituted alicyclic hydrocarbons of typically $C_3$ to $C_{16}$, $C_4$ to $C_{14}$, $C_5$ to $C_{12}$, $C_6$ to $C_{10}$, or $C_7$ to $C_8$, and specifically includes, but is not limited to, cyclopropane, cyclobutane, cyclopentane, cyclohexane, and cycloheptane, may also be oxidatively dehydrogenated using the composite catalyst of the present disclosure. In certain embodiments, the alkane may be sourced from other industrial processes such as those used in the petrochemical industry. Feedstocks generated from petroleum including, but not limited to, paraffin, liquefied petroleum gas (LPG, or liquid petroleum gas), ethane, propane, butane, naphtha, pet naphtha, pygas, light pygas, and gas oil may serve as substrates for the method of oxidatively dehydrogenation using the composite catalyst described herein.

The performance of the oxidative dehydrogenation can be modulated by adjusting conditions including, but not limited to, ratio of oxidant/reactant, temperature, pressure, catalyst loading, and/or reaction time.

In one or more embodiments, a molar ratio of the oxidant to a total amount of the alkane (e.g. n-butane) and/or the alkene (e.g. 1-butene, 2-butene including (Z)-but-2-ene and (E)-but-2-ene) present in the feed mixture ranges from 0.1:1 to 8:1, preferably from 0.5:1 to 6:1, preferably from 1:1 to 4:1, preferably from 2:1 to 3:1. In a preferred embodiment, the oxidant is $O_2$. Other oxidants such as air may be useful for the present disclosure. In one or more embodiments, the feed mixture further comprises an inert gas such as $N_2$, Ar, and/or He. In a preferred embodiment, a $N_2$ stream is mixed with the oxidant (e.g. $O_2$) and the alkane and/or the alkene before the oxidative dehydrogenation process.

In a preferred embodiment, the oxidative dehydrogenation of the alkane and/or the alkene to the corresponding diene is carried out by flowing the feed mixture at a flow rate of 5-200 mL/min, 10-100 mL/min, 20-50 mL/min, or 25-35 mL/min. In a preferred embodiment, the feed mixture is flowed at a temperature in the range of 250–700° C., preferably 300-650° C., preferably 350-600° C., preferably 360-550° C., preferably 370-525° C., preferably 380-500° C., or about 400° C., and preferably at a pressure of 35-350 kPa, 50-300 kPa, 75-200 kPa, or 100-150 kPa.

In a preferred embodiment, the catalyst loading or amount of the composite catalyst present in the oxidative dehydrogenation reaction is in the range of 0.01-1.0 g of catalyst per mL of n-butane feed injected, preferably 0.05-0.8 g/mL, preferably 0.1-0.6 g/mL, preferably 0.2-0.4 g of catalyst per mL of the feed mixture injected. The conditions may vary from these ranges and still provide acceptable conditions for performing the oxidative dehydrogenation process utilizing the composite catalyst of the present disclosure.

Oxidative dehydrogenation catalysts are evaluated for their percent conversion of the alkane/alkene as well as their selectivity to a product (i.e. the corresponding alkene, diene, or $CO_x$ such as CO and/or $CO_2$). When n-butane is used as the feed, the selectivity of the composite catalyst to dehydrogenation products (DH, consisting essentially of 1-butene, 2-butenes and 1,3-butadiene (BD)), oxygenate and cracked products OC (carboxylic acids, ethylene, propylene, methane, and $CO_2$) and partial oxidation products PO (CO and $H_2$) are summarized in Tables 1 and 2. When 1-butene or 2-butene is used as the feed, the selectivity of the composite catalyst to dehydrogenation products (DH, consisting essentially of 1-butene, 2-butenes and 1,3-butadiene (BD)), oxygenate and cracked products OC (e.g., carboxylic acids, ethylene, propylene, methane, and $CO_2$) and partial oxidation products PO (e.g. CO) are summarized in Tables 2-4.

The definitions used in calculating the conversion and selectivity represented for the process of the present disclosure using the oxidative dehydrogenation catalyst are specified in formula (I) and formula (II), respectively.

$$(I): \text{Conversion of feed} = \frac{\text{Moles of feed converted}}{\text{Moles of feed flown}} \times 100\%$$

$$(II): \text{Selectivity to product} = \frac{\text{Moles of product}}{\text{Moles of feed reacted} - \text{Moles of product}} \times 100\%$$

Compared to conventional silica, mesoporous silica species have ordered pore structures, large surface areas, well-defined pore sizes, and thick pore walls, which may enhance dispersion of active catalysts thereby generating a large number active sites and makes the catalyst reach a satisfactory overall catalytic activity.

In one or more embodiments, the feed mixture comprises n-butane, and the process of the present disclosure has an oxidative dehydrogenation n-butane conversion rate of up to 60%, preferably up to 50%, preferably up to 40%, preferably up to 35%, such as for example 28-50%, preferably 30-45%, preferably 32-38%, and at least 20%, preferably at least 22%, preferably at least 24%, preferably at least 26%, preferably at least 30% (see Tables 1-2).

In one or more embodiments, the feed mixture comprises n-butane, and the process of the present disclosure has a butadiene yield of up to 40 wt %, preferably up to 30 wt %, preferably up to 20 wt %, preferably up to 15 wt %, preferably up to 10 wt % relative to a weight of n-butane in the feed mixture, such as for example 8-35 wt %, preferably 12-25 wt %, more preferably 14-20 wt % relative to a weight of n-butane in the feed mixture, and at least 9 wt %, preferably at least 13 wt %, more preferably at least 15 wt % relative to a weight of n-butane in the feed mixture (see Tables 1-2). In a related embodiment, the feed mixture comprises n-butane, and the process further forms butenes with a molar ratio of butadiene to butenes (e.g. 1-butene and 2-butenes) in a range of about 1:1 to about 4:1, preferably about 1.2:1 to about 3:1, preferably about 1.4:1 to about 2.2:1, preferably about 1.7:1 to about 2:1 (see Tables 1-2).

In one or more embodiments, the feed mixture comprises 2-butene, and the process of the present disclosure has an oxidative dehydrogenation 2-butene conversion rate of up to 90%, preferably up to 80%, preferably up to 70%, preferably up to 60%, such as for example 41-83%, preferably 45-71%, preferably 57-69%, and at least 40%, preferably at least 50%, preferably at least 65%, preferably at least 70%, preferably at least 75% (see Tables 2-4).

In one or more embodiments, the feed mixture comprises 2-butene, and the process of the present disclosure has a butadiene yield of up to 85 wt %, preferably up to 80 wt %, preferably up to 70 wt %, preferably up to 60 wt %, preferably up to 50 wt % relative to a weight of 2-butene in the feed mixture, such as for example 30-75 wt %, preferably 49-60 wt %, more preferably 55-59 wt % relative to a weight of 2-butene in the feed mixture, and at least 29 wt %, preferably at least 45 wt %, more preferably at least 50 wt % relative to a weight of 2-butene in the feed mixture (see Tables 2-4).

In one embodiment, the process of the present disclosure performed by flowing a feed mixture at a temperature in a range of 425-550° C., 440-525° C., or about 450° C. may lead to a butadiene yield 10-40% greater, preferably 15-30% greater, more preferably 20-25% greater than a substantially similar process performed by flowing a feed mixture at a temperature in a range of 325-420° C., 350-410° C., or about 400° C.

In one embodiment, the process of the present disclosure performed by adopting a molar ratio of the oxidant (e.g. $O_2$) to a total amount of the alkane (e.g. n-butane) and/or the alkene (e.g. 1-butene, 2-butene including (Z)-but-2-ene and (E)-but-2-ene) present in the feed mixture in a range of 1:3 to 3:1, 1:2 to 2:1, or 2:3 to 1:1 may lead to a butadiene yield 25-85% greater, preferably 35-70% greater, more preferably 50-60% greater than a substantially similar process performed by adopting a molar ratio of the oxidant to a total amount of the alkane and/or the alkene present in the feed mixture in a range of 7:2 to 6:1, 4:1 to 11:2, or 9:2 to 5:1.

The process disclosed herein also demonstrates high selectivity to butadiene (BD) production and suppressed oxygenate and cracked (OC) formation. In some embodiment, the feed mixture comprises n-butane, and the process of the present disclosure has a selectivity ratio of BD production to OC formation ranging from 1.7:1 to 4:1, preferably 2.0:1 to 3.2:1, more preferably from 2.2:1 to 2.8:1, even more preferably from 2.4:1 to 2.6:1 (see Tables 1-2). In a related embodiment, the composite catalyst has a weight ratio of bismuth atoms to the transition metal atoms (e.g. nickel) ranging from 0.7:1 to 1.8:1, preferably 0.9:1 to 1.6:1, preferably 1.2:1 to 1.5:1, or about 1.4:1, and the process has a selectivity ratio of BD production to OC formation that is at least 22% greater, preferably at least 30% greater, more preferably at least 40% greater, even more preferably at least 50% greater, yet even more preferably at least 65% greater than that of a substantially similar process using a composite catalyst having a weight ratio of bismuth atoms to the transition metal atoms (e.g. nickel) less than 0.6:1, for example ranging from 0.1:1 to 0.55:1, 0.2:1 to 0.5:1, or 0.3:1 to 0.4:1, or greater than 1.9:1, for example ranging from 1.95:1 to 4:1, 2:1 to 3.5:1, or 2.5:1 to 3:1. In other embodiments, the feed mixture comprises 2-butene, and the process of the present disclosure has a selectivity ratio of BD production to OC formation ranging from 25:1 to 125:1, preferably 40:1 to 100:1, more preferably from 50:1 to 75:1, even more preferably from 60:1 to 65:1 (see Tables 2-4).

In a preferred embodiment, the reactor is a fixed bed reactor. As used herein, a fixed bed reactor is a type of reaction device that contains a catalyst, usually in pallet form, packed in one or more static beds. In this type of reactor, a feed stream is passed through static beds where reactions occur as the feed stream contacts the catalyst. In a fixed-bed reactor, the static beds are usually held in place and do not move with respect to the reactor. It is equally envisaged that the process of the present disclosure may be adapted to be performed in a fluidized bed reactor. In a fluidized bed reactor, a fluid (gas or liquid) is passed through a granular solid material (usually a catalyst, preferably spherically shaped) at high enough velocities to suspend the solid and cause it to behave as though it were a fluid.

The examples below are intended to further illustrate protocols for preparing and characterizing the composite catalysts of the present disclosure. Further, they are intended to illustrate analyzing the properties and performance of these composite catalysts. They are not intended to limit the scope of the claims.

Example 1

Experimental: General

All catalysts were prepared by co-impregnation technique and calcined in a two-step procedure, i.e. calcined at 350° C. for 1 h, and at 590° C. for 2 h. The extent of formation of this new mesoporous composite material depends on the type of support used as well as the loading of the Ni and Bi nitrates solution.

The catalyst samples were characterized by identifying the new material phase using powder X-ray diffraction (XRD). X-ray diffraction patterns of calcined samples were recorded from (2 theta) range of 5° to 90° using Rigaku Miniflex II desktop X-ray diffractometer and using Cu Kα radiation (wavelength λ=1.5406 Å) with 30 mA and 40 kV as operating parameters, a step size of 0.02° and a speed of 0.5°/min. 2θ=25 to 35° was chosen to precisely examine the phases of Bi oxide in different catalysts. All the characteristic peaks associated with this new material phase have been identified in the silica sol supported catalyst and the mesoporous (SBA-15 and silica foam) supported catalysts. The new $Bi_2SiO_5$ phase showed peaks at 2θ=28.95°, 32.33°, and 33.38° with (3,1,1), (0,2,0), and (0,0,2) diffraction lines.

α-$Bi_2O_3$ and β-$Bi_2O_3$ are preferred candidates for the composite catalyst disclosed herein which additionally comprises $Bi_2O_3$. $Bi_2O_3$/$Bi_2SiO_5$ species formed on mesoporous $SiO_2$ is also a preferable mesoporous layered composite of the present disclosure. The mesoporous $SiO_2$ is derived from substantially silicone oxide(s). At least one of SBA-15, silica foam and silica sol is preferable as the silicone oxide. SBA-15 and silica foam are most preferable because of their mesoporosity.

The present disclosure is related to a mesoporous composite made from bismuth species and silicon oxide(s). The mesoporous composite contains at least $Bi_2SiO_5$ and mesoporous silica. Bismuth precursors containing bismuth species that eventually form the $Bi_2SiO_5$ phase are commercially available. One example is water-soluble bismuth nitrate, which makes the $Bi_2SiO_5$ phase when mixed with silicon oxide(s), preferably mesoporous silica.

Preferably, at least one oxide of a metal element from the groups VIB, VIIB, and VIIIB in the periodic table is added to the mesoporous composite to form the catalyst. The metal element may be Ni, Fe, Co, other transition metal elements, or a combination of these metal elements. The process for oxidative dehydrogenation is an application that utilizes this composite material as catalyst. Through the oxidative dehydrogenation, saturated hydrocarbon is converted to unsaturated hydrocarbon. The saturated hydrocarbon and the unsaturated hydrocarbon can be selected from paraffins ranging from $C_2$ to $C_8$ and olefins of the same carbon number as the paraffins.

Example 2

Preparation of 20 wt % Ni 30 wt % Bi/Mesoporous SBA-15

A calculated amount of Ni precursor was weighed and dissolved in deionized water. After complete dissolution, an appropriate amount of Bi precursor was added and stirred. 2 g of dried SBA-15 support was added for impregnation and left overnight for equilibrium Bi species adsorption. The sample mixture was dried via evaporation at 80° C. for enforced Ni species deposition. The solid product obtained was further dried at 120° C. in an oven for 3 h. After calcination, this catalyst showed a pure phase of the new mesoporous composite material ($Bi_2SiO_5$), as shown by XRD measurement in FIG. 1.

Example 3

Preparation 20 wt % Ni 10 wt % Bi/SBA-15 and 14 wt % Ni 10 wt % Bi/SBA-15

Each calculated amount of Ni precursor was weighed and dissolved in deionized water. After complete dissolution, each appropriate amount of Bi precursor was added and stirred. 2 g of dried SBA-15 support was added for impregnation and left overnight for equilibrium Bi species adsorption. The sample mixtures were dried via evaporation at 80° C. for enforced Ni species deposition. The solid products obtained were further dried at 120° C. in an oven for 3 h. After calcination, the 20 wt % Ni 10 wt % Bi/SBA-15 catalyst showed a combination of phases of the new mesoporous composite material ($Bi_2SiO_5$) and β-$Bi_2O_3$ as shown by XRD measurement in FIG. 1. The same phases were observed with the 14 wt % Ni 10 wt % Bi/SBA-15 catalyst.

Example 4

Preparation of 20 wt % Ni 30 wt % Bi/Mesoporous Silica Foam

A calculated amount of Ni precursor was weighed and dissolved in deionized water. After complete dissolution, an appropriate amount of Bi precursor was added and stirred. 2 g of dried mesoporous silica foam support was added for impregnation and left overnight for equilibrium Bi species adsorption. The sample mixture was dried via evaporation at 80° C. for enforced Ni species deposition. The solid product obtained was further dried at 120° C. in an oven for 3 h. After calcination, this catalyst showed an almost pure phase of the new mesoporous composite material ($Bi_2SiO_5$) as shown by XRD measurement in FIG. 1.

Example 5

Preparation of 20 wt % Ni 30 wt % Bi/Silica Sol

A calculated amount of Ni precursor was weighed and dissolved in deionized water. After complete dissolution, an appropriate amount of Bi precursor was added and stirred. 2 g of dried silica sol support was added for impregnation and left overnight for equilibrium Bi species adsorption. The sample mixture was dried via evaporation at 80° C. for enforced Ni species deposition. The solid product obtained was further dried at 120° C. in an oven for 3 h. After calcination, this catalyst showed an almost pure phase of the new mesoporous composite material ($Bi_2SiO_5$) as shown by XRD measurement in FIG. 1.

Example 6

Preparation of 30 wt % Bi/SBA-15

A calculated amount of Bi precursor was weighed and dissolved in deionized water. After dissolution, 2 g of dried SBA-15 support was added for impregnation and left overnight for equilibrium Bi species adsorption. The sample mixture was dried via evaporation at 80° C. The solid product obtained was further dried at 120° C. in an oven for 3 h. After calcination, this catalyst showed a combination of phases of the new mesoporous composite material ($Bi_2SiO_5$) and $\beta$-$Bi_2O_3$ as shown by XRD measurement in FIG. 1.

Example 7

Catalyst Evaluation

The performance of the prepared catalysts was tested in a fixed-bed reactor, and the results for the case of n-butane feed are presented in Table 1.

TABLE 1

Catalytic performance of the catalysts in n-butane conversion

| Catalyst Support | 20Ni-30Bi SBA-15 Example 1 | 20Ni-10Bi SBA-15 Example 2 | 20Ni-30Bi $SiO_2$ foam Example 3 | 20Ni-30Bi $SiO_2$ sol Example 4 |
|---|---|---|---|---|
| $n$-$C_4H_{10}$ conversion [%] | 28.9 | 30.0 | 29.2 | 35.6 |
| Selectivity[1] [C %] | | | | |
| DH | 75.2 | 71.8 | 77.6 | 78.3 |
| 2-$C_4H_8$ | 15.4 | 14.6 | 17.2 | 18.6 |
| 1-$C_4H_8$ | 12.3 | 7.8 | 14.8 | 18.1 |
| BD | 47.5 | 49.4 | 45.6 | 41.6 |
| PO | 24.8 | 28.2 | 22.4 | 21.6 |
| OC | 19.7 | 28.2 | 21.0 | 20.5 |
| CO | 5.1 | 0.0 | 1.4 | 1.1 |
| BD yield | 13.7 | 14.8 | 13.3 | 14.8 |

[1] DH: dehydrogenation, BD: butadiene, OC: oxygenate and the cracked, PO: partial oxidation.
[2] selectivity at $1^{st}$ step dehydrogenation,
[3] selectivity at $2^{nd}$ step dehydrogenation Similarly, butenes were utilized as feed and the catalysts performance results are presented in Table 2. The reaction temperature in all the tests was in the range of 400–500° C. and $O_2$/feed ratio ranged from 1.0 to 4.0 mol/mol.

TABLE 2

Catalytic performance of the 14 wt % Ni 10 wt % Bi/SBA-15 catalysts using different feeds (n-butane, 1-butene and 2-butene) at $O_2$/feed = 2.0 mol/mol and 450° C.

| Catalyst Support Feed | 14Ni-10Bi SBA-15 $n$-$C_4H_{10}$ | 14Ni-10Bi SBA-15 1-$C_4H_8$ | 14Ni-10Bi SBA-15 2-$C_4H_8$ |
|---|---|---|---|
| Feed conversion [%] | 27.7 | 44.7 | 69.0 |
| Selectivity[1] [C %] | | | |
| DH* | 78.4 | 96.2 | 91.2 |
| 2-$C_4H_8$ | 15.0 | 26.1 | — |
| 1-$C_4H_8$ | 10.2 | — | 5.6 |
| BD | 53.2 | 70.1 | 85.6 |
| PO | 21.6 | 3.8 | 8.8 |
| OC | 17.1 | 0.6 | 2.1 |
| CO | 4.5 | 3.2 | 6.7 |
| BD yield | 14.7 | 31.3 | 59.0 |

DH*: Dehydrogenation and isomerization

The effect of temperature and oxygen/feed ratio on the conversion and product selectivity are summarized in Tables 3 and 4, respectively.

TABLE 3

Catalytic performance of the 14 wt % Ni 10 wt % Bi/SBA-15 catalysts using different 2-butene feed at $O_2$/feed = 2.0 mol/mol and 400-500° C.

| Catalyst Support Temperature [° C.] | 14Ni-10Bi SBA-15 400 | 14Ni-10Bi SBA-15 450 | 14Ni-10Bi SBA-15 500 |
|---|---|---|---|
| Feed conversion [%] | 57.0 | 69.0 | 71.3 |
| Selectivity[1] [C %] | | | |
| DH | 95.3 | 91.2 | 86.2 |
| 2-$C_4H_8$ | — | — | — |
| 1-$C_4H_8$ | 10.0 | 5.6 | 5.1 |
| BD | 85.3 | 85.6 | 81.1 |
| PO | 4.7 | 8.8 | 13.8 |
| OC | 1.5 | 2.1 | 3.1 |
| CO | 3.2 | 6.7 | 10.7 |
| BD yield | 48.6 | 59.0 | 57.8 |

DH*: Dehydrogenation and isomerization

TABLE 4

Catalytic performance of the 14 wt % Ni 10 wt % Bi/SBA-15 catalysts using different 2-butene feed at $O_2$/feed = 1.0-4.0 mol/mol and 450° C.

| Catalyst Support $O_2$/2-$C_4H_8$ ratio | 14Ni-10Bi SBA-15 1.0 | 14Ni-10Bi SBA-15 2.0 | 14Ni-10Bi SBA-15 4.0 |
|---|---|---|---|
| Feed conversion [%] | 40.8 | 57.0 | 83.3 |
| Selectivity[1] [C %] | | | |
| DH* | 96.9 | 95.3 | 91.9 |
| 2-$C_4H_8$ | — | — | — |
| 1-$C_4H_8$ | 24.6 | 10.0 | 2.6 |
| BD | 72.2 | 85.3 | 89.3 |
| PO | 3.2 | 4.7 | 8.2 |
| OC | 1.1 | 1.5 | 3.2 |
| CO | 2.1 | 3.2 | 5.0 |
| BD yield | 29.5 | 48.6 | 74.4 |

DH*: Dehydrogenation and isomerization.

A total of 300 mg of the prepared catalyst was used and an online gas chromatograph (GC) was used for product analysis. The combination of the new mesoporous composite material ($Bi_2SiO_5$) and $\beta$-$Bi_2O_3$ showed an enhanced ability in stabilizing the reducibility of the active metal oxide (NiO for this application), thereby improving the activity and selectivity of desired butadiene product. A high yield of 74% butadiene was achieved over 14 wt % Ni 10 wt % Bi/SBA-15 catalyst at 400° C. reaction temperature.

The invention claimed is:

1. A composite catalyst, comprising:
   a mesoporous silica support which is at least one selected from the group consisting of SBA-15, mesoporous silica foam, and silica sol; and
   a catalytic material comprising a bismuth silicate and a transition metal oxide impregnated on the mesoporous silica support,
   wherein the composite catalyst is devoid of molybdenum.

2. The composite catalyst of claim 1, wherein the bismuth silicate is $Bi_2SiO_5$.

3. The composite catalyst of claim 1, wherein the transition metal oxide is at least one selected from the group consisting of nickel(II) oxide, iron(II) oxide, and cobalt(II) oxide.

4. The composite catalyst of claim 1, wherein the transition metal oxide is nickel(II) oxide.

5. The composite catalyst of claim 1, which comprises 5-40 wt % of bismuth atoms and 10-30 wt % of transition metal atoms, each relative to a weight of the mesoporous silica support.

6. The composite catalyst of claim 1, wherein the catalytic material further comprises bismuth oxide.

7. A method of preparing the composite catalyst of claim 1, the method comprising:
   mixing a transition metal salt and a bismuth salt in a solvent to form a first mixture;
   mixing the first mixture and the mesoporous silica support to form a second mixture;
   drying the second mixture to form a dried mass; and
   calcining the dried mass in air thereby producing the composite catalyst.

8. The method of claim 7, wherein the transition metal oxide is nickel(II) oxide, and wherein the transition metal salt is nickel(II) nitrate.

9. The method of claim 7, wherein the bismuth salt is bismuth(III) nitrate.

10. The method of claim 7, wherein the solvent comprises water.

11. The method of claim 7, wherein the second mixture is dried at a temperature ranging from 50° C. to 200° C.

12. The method of claim 7, wherein the dried mass is calcined in air at a temperature ranging from 300° C. to 700° C.

13. A process of oxidatively dehydrogenating an alkane and/or an alkene to a corresponding diene, the process comprising:
   flowing a feed mixture comprising the alkane and/or the alkene, and an oxidant through a reactor loaded with the composite catalyst of claim 1, thereby forming the corresponding diene.

14. The process of claim 13, wherein the alkane is n-butane, the alkene is a butene, and the corresponding diene is butadiene.

15. The process of claim 13, wherein a molar ratio of the oxidant to a total amount of the alkane and/or the alkene ranges from 0.1:1 to 8:1.

16. The process of claim 13, wherein the flowing is performed at a temperature ranging from 250° C. to 700° C.

17. The process of claim 13, wherein the oxidant is $O_2$.

18. The process of claim 14, wherein the feed mixture comprises n-butane, and wherein the process has a butadiene yield of 10-20 wt % relative to a weight of n-butane.

19. The process of claim 14, wherein the feed mixture comprises n-butane, and wherein the process further forms butenes with a molar ratio of butadiene to butenes ranging from 1:1 to 3:1.

20. The process of 14, wherein the feed mixture comprises 2-butene, and wherein the process has a butadiene yield of 30-80 wt % relative to a weight of 2-butene.

* * * * *